United States Patent [19]

Behre et al.

[11] Patent Number: 5,248,812
[45] Date of Patent: Sep. 28, 1993

[54] PROCESS FOR THE ISOLATION OF 2-NAPHTHYLAMINE-1,5-DISULPHONIC ACID

[75] Inventors: Horst Behre, Odenthal-Eikamp; Heinz-Ulrich Blank, Odenthal-Glöbusch; Holger Heidenreich, Kuden; Fritz Pohl, Brunsbuettel; Paul Uhrhan, Leverkusen, all of Fed. Rep. of Germany

[73] Assignee: Bayer Aktiengesellschaft, Leverkusen, Fed. Rep. of Germany

[21] Appl. No.: 939,194

[22] Filed: Sep. 2, 1992

[30] Foreign Application Priority Data

Sep. 12, 1991 [DE] Fed. Rep. of Germany ....... 4130333

[51] Int. Cl.⁵ ................... C07C 303/02; C07C 303/22
[52] U.S. Cl. ..................................... 562/124; 562/68; 562/72
[58] Field of Search ............... 562/124, 72, 68

[56] References Cited

U.S. PATENT DOCUMENTS 4,348,336  9/1982  Blank et al. ........................... 562/72
4,407,762  10/1983  Blank et al. ........................... 562/72
4,551,283  11/1985  Blattner ................................. 562/72

Primary Examiner—Marianne M. Cintins
Assistant Examiner—Michael B. Hydorn
Attorney, Agent, or Firm—Sprung Horn & Woods

[57] ABSTRACT

When 2-naphthylamine-1,5-disulphonic acid is precipitated from the as-sulphonated reaction mixtures by dilution, a purer product is obtained, with a low level of adherent sulphuric acid, if the precipitation by dilution of the reaction mixture is carried out under precisely defined conditions.

11 Claims, No Drawings

PROCESS FOR THE ISOLATION OF 2-NAPHTHYLAMINE-1,5-DISULPHONIC ACID

The invention relates to the isolation from sulphonation mixtures containing it, of 2-naphthylamine-1,5-disulphonic acid ("sulpho Tobias acid") in improved quality.

2-Naphthylamine-1,5-disulphonic acid is an important product for the preparation of dyestuffs, in particular of reactive dyestuffs. It can be prepared from 2-naphthylamine-1-sulphonic acid ("Tobias acid") by sulphonation in fuming sulphuric acid ("oleum") having an $SO_3$ content of 15 to 30% by weight, for example at room temperature.

The 2-naphthylamine-1,5-disulphonic acid can be precipitated from the resulting reaction mixtures by dilution. This precipitation of the free acid has the disadvantage that the 2-naphthylamine-1,5-disulphonic acid isolated as the free acid is contaminated by decomposition products such as 2-naphthylamine and 2-naphthylamine-5-sulphonic acid (see Bucherer and Wahl, J. pr. Chemie 103, 151 (1921); "Methoden der organischen Chemie" (Methods of Organic Chemistry), (Houben-Weyl), vol. 9, Georg Thieme Verlag, Stuttgart 1955, pp. 481-484; Donaldson, The Chemistry and Technology of Naphthalene Compounds, Edward Arnold (Publishers) LTD., London 1957; Armstrong, Wynne, Chem. New 62, 163 (1890)) and precipitates in a crystalline form in which it contains substantial amounts (15-20% by weight) of sulphuric acid. This sulphuric acid content of the separated 2-naphthylamine-1,5-disulphonic acid can be reduced by washing with water or highly dilute sulphuric acid but only at the cost of high losses in yield due to the high solubility of the 2-naphthylamine-1,5-disulphonic acid in water and dilute sulphuric acid.

It has now been found that the difficulties arising with the precipitation of 2-naphthylamine-1,5-disulphonic acid in the form of the free acid can be avoided by carrying out the precipitation by dilution of the reaction mixtures under precisely defined conditions.

The invention relates to a process for the isolation of 2-naphthylamine1,5-disulphonic acid from a reaction mixture containing, relative to the entire reaction mixture, 15 to 35, preferably 20 to 30% by weight of 2-naphthylamine-1,5-disulphonic acid and 65 to 85, preferably 70 to 80% by weight of sulphuric acid or oleum having an $SO_3$ content, relative to sulphuric acid + $SO_3$, of 1 to 20, preferably 10 to 17% by weight, by (a) diluting the reaction mixture with dilute sulphuric acid and water to a sulphuric acid content, relative to sulphuric acid and water, of 20 to 80, preferably 35 to 55, particularly preferably 40 to 50 and in particular 45 to 48% by weight, while (b) maintaining a temperature of 30° to 80°, preferably 35° to 70°, particularly preferably 45° to 65° and in particular 54° to 59° C., such that (i) the ratio of added sulphuric acid to sulphuric acid originally present—calculated as 100% pure sulphuric acid—is at least 0.3, preferably at least 0.5, in particular at least 0.75, and (ii) the sulphuric acid content during the entire dilution process—assuming ideal mixing—does not fall below the lower limit of range (a) by more than 10%.

An essential requirement for the invention to work is thus—in addition to the temperature—not only the sulphuric acid content at the end of the process but evidently also the avoidance of temporarily too low sulphuric acid concentrations, as appear transiently for example when the reaction mixture is run into water. According to the invention, the preferred procedure is therefore such that, upon dilution, the sulphuric acid content of the reaction mixture, if possible, does not pass through a minimum or only passes through a minimum which is close to the final value of the sulphuric acid content.

In principle, the process according to the invention can be carried out in such a manner that the reaction mixture to be diluted and water are added to a dilute sulphuric acid whose concentration corresponds at least to the minimum sulphuric acid content required by the claims.

In a preferred embodiment, the reaction mixture, water and dilute sulphuric acid are metered in simultaneously such that the desired concentration is established and kept virtually constant during the entire mixing process.

Instead of fresh dilute sulphuric acid, it is also possible to use for the dilution sulphuric acid from a previous batch ("mother acid") remaining after precipitation of 2-naphthylamine-1,5-disulphonic acid. Such a "mother acid" contains, relative to the sum of water and sulphuric acid, in general 20 to 80, preferably 35 to 55, particularly preferably 40 to 50 and in particular 45 to 48% by weight of sulphuric acid and, relative to sulphuric acid, 0.1 to 3.0, preferably 0.5 to 1.5.% by weight of 2-naphthylamine-1,5-disulphonic acid, 0.01 to 1.0, preferably 0.05 to 0.2% by weight of 2-naphthylamine-1,6-disulphonic acid and 0.01 to 1.0, preferably 0.05 to 0.2% by weight of 2-naphthylamine-1,7-disulphonic acid. It has been found that the use of mother acid instead of pure dilute sulphuric acid leads to improved filterability and to a lower sulphuric acid content of the isolated product.

The heat generated during the dilution process is removed by suitable cooling.

In the process according to the invention, the 2-naphthylamine-1,5-disulphonic acid is obtained in a readily filterable form; the 2-naphthylamine-1,5-disulphonic acid content is in the range above 65% by weight, relative to moist product (above 80% by weight calculated for dry product), and the sulphuric acid content, relative to moist product, is between 8 and 14% by weight (calculated as 100% pure $H_2SO_4$) (between 9 and 17% by weight, calculated for dry product).

It has proven advantageous to leave the precipitated 2-naphthylamine-1,5-disulphonic acid in the dilute solution for another 0.1 to 10, preferably 0.2 to 5, in particular 0.5 to 2 hours at temperatures of 20° to 55° C., preferably 30° to 45° C. before separating off the product.

The process according to the invention can be carried out batchwise or continuously.

The percentages given in the Examples which follow are by weight.

EXAMPLES

Example 1

600 g of 50% strength aqueous sulphuric acid are initially introduced into a 2 liter 5-neck flask equipped with sickle stirrer, 2 metering dropping funnels, condenser and internal thermometer, and heated to 40° C.

500 g of sulphonation mixture obtained by reaction of 2-naphthylamine-1-sulphonic acid (Tobias acid) with oleum ($SO_3$ content: 25%) at 20° C. (2-naphthylamine-1,5-disulphonic acid content: 23.4%; 2-naphthylamine-1,6-disulphonic acid content: 1.5%; 2-naphthylamine- 1,7-disulphonic acid content: 0.3%; balance to 100%: sulphuric acid, sulphur trioxide, organic byproducts of unknown structure) and 500 g of water are run in simultaneously at 40° C. over a period of about 4 hours with cooling. The resulting crystalline suspension, which settles very readily, is additionally stirred at 40° C. for about 1 hour, cooled to about 20° C. over a period of several hours while stirring is continued, after which stirring at 20° C. is continued for several hours. The very readily filterable product is filtered off with suction through a sintered glass filter and washed with 125 g of 50% strength aqueous sulphuric acid in order to displace any adhering mother acid. This gives (average value from 6 experiments with 5 recycled run-offs)

160 g of moist 2-naphthylamine-1,5-disulphonic acid and 1535 g of run-off+wash acid, 600 g of which are recycled. The isolated product contains on average (HPLC):

| | |
|---|---|
| 69.9% | of 2-naphthylamine-1,5-disulphonic acid, |
| 3.2% | of 2-naphthylamine-1,6-disulphonic acid, |
| <0.05% | of 2-naphthylamine-1-sulphonic acid. |
| <0.05% | of 2-naphthylamine-5-sulphonic acid. |
| <0.05% | of 2-naphthylamine-8-sulphonic acid. |
| 0.05% | of 2-naphthylamine-1,7-disulphonic acid. |
| 11.1% | of sulphuric acid and |
| 15.4% | of water |
| Σ99.6% | The yield is 95% of theory, relative to 2-naphthylamine-1,5-disulphonic acid used (in the form of the sulphonation mixture). |

Example 2

293 g of Tobias acid (content: 99.5%) are sulphonated with 1,240 g of oleum ($SO_3$ Content: 25%) at a temperature of 18°–200° C. with immediate removal of the heat of reaction. After a residence time of 1 hour at 20° C., the reaction mixture has the following composition:

| | |
|---|---|
| 2-Naphthylamine-1,5-disulphonic acid | 24.7% |
| 2-Naphthylamine-1,6-disulphonic acid | 0.8% |
| 2-Naphthylamine-1,7-disulphonic acid | 0.3% |
| 2-Naphthylamine-1-sulphonic acid | 0.1% |
| Sulphuric acid | 61.0% |
| $SO_3$ | 12.2% |
| | Σ100.1% |

1580 g of water and 1840 g of 50% strength aqueous sulphuric acid are simultaneously and continuously combined with 1533 g of the reaction mixture at 40° C. After about 24 hours at 40° C., the mixture is filtered, giving 562 g of a colourless filter cake of the following composition:

| | |
|---|---|
| 2-Naphthylamine-1,5-disulphonic acid | 66.0% |
| 2-Naphthylamine-1,6-disulphonic acid | 1.2% |
| 2-Naphthylamine-1,7-disulphonic acid | 0.4% |
| 2-Naphthylamine-1-sulphonic acid | 0.1% |
| Water | 19.5% |
| Sulphuric acid | 13.5% |
| | Σ100.2% |

Example 3

1533 g of the reaction mixture prepared in Example 2 are diluted continuously and simultaneously with 1580 g of water and 1840 g of recycled mother acid from Example 2 at 58° C. After a residence time of 1 hour at 58° C., the partially precipitated suspension is discharged into a further stirred container and cooled to about 40° C. over a period of 1 hour. After stirring for another 23 hours, the suspension is filtered, giving 488 g of a colourless, granular filter cake of the following composition:

| | |
|---|---|
| 2-Naphthylamine-1,5-disulphonic acid | 75.9% |
| 2-Naphthylamine-1,6-disulphonic acid | 1.8% |
| 2-Naphthylamine-1,7-disulphonic acid | 0.4% |
| 2-Naphthylamine-1-sulphonic acid | 0.05% |
| Water | 13.6% |
| Sulphuric acid | 8.1% |
| | Σ99.85% |

Comparison 1533 g of the reaction mixture prepared in Example 2 are diluted continuously with 1580 g of water at 40° C. without addition of dilute sulphuric acid. After a residence time of 24 hours, the suspension is filtered, giving 638 g of a colourless felt-like filter cake of the following composition:

| | |
|---|---|
| 2-Naphthylamine-1,5-disulphonic acid | 58.1% |
| 2-Naphthylamine-1,6-disulphonic acid | 1.5% |
| 2-Naphthylamine-1,7-disulphonic acid | 0.6% |
| 2-Naphthylamine-5-sulphonic acid | 0.1% |
| 2-Naphthylamine-1-sulphonic acid | 0.1% |
| Water | 19.5% |
| Sulphuric acid | 19.6% |
| | Σ100.0% |

We claim:

1. Process for the isolation of 2-naphthylamine-1,5-disulphonic acid from a reaction mixture containing, relative to the entire reaction mixture, 15 to 35% by weight of 2-naphthylamine-1,5-disulphonic acid and 65 to 85% by weight of sulphuric acid or oleum having an $SO_3$ content, relative to sulphuric acid+$SO_3$, of 1 to 20% by weight, by (a) diluting the reaction mixture with dilute sulphuric acid and water to a sulphuric acid content, relative to sulphuric acid and water, of 20 to 80% by weight, while (b) maintaining a temperature of 30° to 80° C., such that (i) the ratio of added sulphuric acid to sulphuric acid originally present—calculated as 100% pure sulphuric acid—is at least 0.3, and (ii) the sulphuric acid content during the entire dilution process does not fall below the lower limit of range (a) by more than 10%.

2. Process according to claim 1, according to which the reaction mixture used has a 2-naphthylamine-1,5-disulphonic acid content of 20 to 30% by weight.

3. Process according to claim 1, according to which the reaction mixture used has a sulphuric acid or oleum content of 70 to 80% by weight.

4. Process according to claim 1, according to which the oleum has an $SO_3$ content of 10 to 17% by weight.

5. Process according to claim 1, according to which the reaction mixture is diluted to a sulphuric acid content of 35 to 55% by weight.

6. Process according to claim 1, according to which the reaction mixture is diluted to a sulphuric acid content of 40 to 50% by weight.

7. Process according to claim 1, according to which the reaction mixture is diluted to a sulphuric acid content of 45 to 48% by weight.

8. Process according to claim 1, according to which the reaction is carried out in a temperature range from 35° to 70° C.

9. Process according to claim 1, according to which the ratio (i) is at least 0.5.

10. Process according to claim 1, according to which dilution is carried out simultaneously with water and dilute sulphuric acid.

11. Process according to claim 1, according to which the mother acid of a previous batch is used instead of dilute sulphuric acid.

* * * * *